United States Patent [19]

Bullwinkel et al.

[11] Patent Number: 5,538,019
[45] Date of Patent: Jul. 23, 1996

[54] SPUNBOND CIGARETTE FILTER

[75] Inventors: Edward P. Bullwinkel, Roswell; Leon E. Chambers, Jr., Cumming; Robert G. Geer, Canton, all of Ga.

[73] Assignee: Schweitzer-Mauduit International, Inc., Alpharetta, Ga.

[21] Appl. No.: 148,078

[22] Filed: Nov. 3, 1993

[51] Int. Cl.⁶ ............................................. A24D 1/04
[52] U.S. Cl. .............................. 131/331; 131/332
[58] Field of Search ........................... 131/331, 332, 131/335

[56] References Cited

U.S. PATENT DOCUMENTS

| | | | |
|---|---|---|---|
| 439,004 | 10/1890 | Harris. | |
| 2,966,156 | 12/1960 | Touey et al. | 131/208 |
| 3,110,642 | 11/1963 | Harrington | 156/28 |
| 3,226,795 | 1/1966 | Swerdloff | 28/72 |
| 3,276,944 | 10/1966 | Levy. | |
| 3,329,544 | 7/1967 | Smith et al. | 156/157 |
| 3,338,992 | 8/1967 | Kinney. | |
| 3,341,394 | 9/1967 | Kinney. | |
| 3,393,685 | 7/1968 | Mumpower, II | 131/267 |
| 3,396,733 | 8/1968 | Allseits et al. | 131/10.5 |
| 3,397,700 | 8/1968 | Harlow et al. | 131/335 X |
| 3,407,822 | 10/1968 | Touey et al. | 131/266 |
| 3,461,882 | 8/1969 | Epstein | 131/262 |
| 3,502,538 | 3/1970 | Petersen. | |
| 3,502,763 | 3/1970 | Hartmann. | |
| 3,509,009 | 4/1970 | Hartmann | 151/150 |
| 3,538,920 | 11/1970 | Davis | 131/10 |
| 3,542,615 | 11/1970 | Dobo et al.. | |
| 3,595,245 | 7/1971 | Buntin | 131/269 |
| 3,608,564 | 9/1971 | Takahashi | 131/266 |
| 3,667,478 | 6/1972 | Waterbury | 131/335 |
| 3,692,618 | 9/1972 | Dorschner et al.. | |
| 3,704,192 | 11/1972 | Soehngen et al.. | |
| 3,749,685 | 7/1973 | Johnson, Jr. | 260/2.5 |
| 3,856,025 | 12/1974 | Sato | 131/264 |
| 3,861,404 | 1/1975 | Changani | 131/269 |
| 3,880,173 | 4/1975 | Hill | 131/269 |
| 3,882,877 | 5/1975 | Brackmann | 131/266 |
| 3,887,730 | 6/1975 | Rainer | 427/244 |
| 3,930,077 | 12/1975 | Levers et al. | 427/384 |
| 3,939,849 | 2/1976 | Baxter | 131/269 |
| 3,978,185 | 8/1976 | Buntin | 264/93 |
| 4,054,550 | 10/1977 | Parker | 264/43.3 |
| 4,059,121 | 11/1977 | Brackmann | 131/269 |
| 4,182,350 | 1/1980 | Steinau | 131/269 |
| 4,232,130 | 11/1980 | Baxter | 521/143 |
| 4,279,848 | 7/1981 | Baxter et al. | 264/53 |
| 4,340,563 | 7/1982 | Appel et al.. | |
| 4,364,403 | 12/1982 | Horsewell et al. | 131/332 |
| 4,366,826 | 1/1983 | Horsewell | 131/336 |
| 4,379,465 | 4/1983 | Coq | 131/332 |
| 4,546,040 | 10/1985 | Knotek | 428/370 |
| 4,729,391 | 3/1988 | Woods et al. | 131/335 X |
| 4,903,714 | 2/1990 | Barnes et al. | 131/335 |
| 4,961,415 | 10/1990 | Radwanski et al. | 131/332 |
| 5,012,829 | 5/1991 | Thesing et al. | 131/335 X |

FOREIGN PATENT DOCUMENTS

| | | |
|---|---|---|
| 0604731 | 7/1994 | European Pat. Off.. |
| 2009251 | 1/1970 | France. |
| 922698 | 4/1963 | United Kingdom. |
| 9220251 | 11/1992 | WIPO. |

OTHER PUBLICATIONS

Japanese Abstract, JP,A06033359 dated Feb. 8, 1994.

*Primary Examiner*—Jennifer Bahr
*Attorney, Agent, or Firm*—Dority & Manning

[57] ABSTRACT

A filter made from a nonwoven spunbond web comprising a plurality of continuous intertwined filaments, each filament having a diameter of about 25 to about 100 microns, predominantly present in the web as loop springs having diameters of about 1 to 3 millimeters. The web is made from a plurality of spunbond filaments laid randomly onto a moving belt. The webs of the present invention find particular utility when formed into cylinders as filters for smoking articles. In the smoking articles, the filters of the invention have a desirable degree of firmness while demonstrating an acceptable pressure drop.

16 Claims, 2 Drawing Sheets

SPUNBOND CIGARETTE FILTER

FIELD OF THE INVENTION

The present invention relates to cigarette filters used in smoking articles. More particularly, the present invention relates to filters made from a web composed of thermoplastic polymer fibers/filaments.

BACKGROUND OF THE INVENTION

Filtered cigarettes are well-known and are a common form of smoking articles. Filtered cigarettes comprise a column of tobacco and, at one end, a filter plug (i.e., a filter). The column of tobacco is wrapped in cigarette paper and the filter plug is joined to the cigarette by tipping paper. Conventional filters are formed either from compressed strips of paper or cellulose acetate tows. However, thermoplastic polymers possess attributes that would suggest they might be converted into materials that could be used as cigarette filters. For example, U.S. Pat. No. 3,595,245 issued to Bunt et al is directed to a meltblown roving of polypropylene fibers formed as a tow and processed into cigarette filters. Also, U.S. Pat. No. 4,546,040 issued to Knotek et al describes other polypropylene filter cigarette filters. Such thermoplastic polymer filament filters, such as those made of polypropylene fibers have achieved little, if any, commercial success. Common deficiencies of such attempts to form thermoplastic filament filters have included inadequate firmness so that the filter end of the cigarette has an uncharacteristic and undesirable softness. Other deficiencies include a greater than desired pressure drop so that the smoker experiences a perceivable increase in draw resistance.

Accordingly, there is a need in the industry for a filter for smoking articles made from a web of synthetic fibers that overcomes the deficiencies present in filters made from previously known thermoplastic and nonwoven filament webs.

DEFINITIONS

As used herein, the term "nonwoven web" refers to a web that has a structure of individual fibers or filaments which are interlaid, but not in an identifiable repeating manner. Nonwoven webs have been, in the past, formed by a variety of processes known to those skilled in the art such as, for example, meltblowing, spunbonding and bonded carded web processes.

As used herein, the term "spunbond web" refers to a web of small diameter fibers and/or filaments which are formed by extruding a molten thermoplastic material as filaments from a plurality of fine, usually circular, orifices in a spinnerette with the diameter of the extruded filaments then being rapidly reduced, for example, by non-eductive or eductive fluid-drawing or other well known spunbonding mechanisms. The production of spunbond nonwoven webs is illustrated in patents such as Appel, et al., U.S. Pat. No. 4,340,563; Dorschner et al., U.S. Pat. No. 3,692,618; Kinney, U.S. Pat. Nos. 3,338,992 and 3,341,394; Levy, U.S. Pat. No. 3,276,944; Peterson, U.S. Pat. No. 3,502,538; Hartman, U.S. Pat. No. 3,502,763; Dobo et al., U.S. Pat. No. 3,542,615; and Harmon, Canadian Patent No. 803,714.

As used herein, the terms "thermoplastic material" and "thermoplastic polymer" refers to a long-chain polymer that softens when exposed to heat and returns to its original condition when cooled to room temperature. Other exemplary thermoplastic materials include, without limitation, polyvinyl chlorides, polyesters, polyamides, polyfluorocarbons, polyolefins, polyurethanes, polystyrenes, polyvinyl alcohols, caprolactams, copolymers of ethylene and at least one vinyl monomer (e.g., poly(ethylene vinyl acetates), copolymers of ethylene and n-butyl acrylate (e.g., ethylene n-butyl acrylates), and cellulosic and acrylic resins.

As used herein, the term "machine direction" refers to the planar dimension of a nonwoven fibrous web which is in the direction of travel of the forming surface onto which fibers are deposited during formation of the web.

As used herein, the term "cross-machine direction" refers to the planar dimension of a nonwoven fibrous web which is in the direction that is perpendicular to the machine direction defined above.

As used herein, the term "polymer" generally includes, but is not limited to, homopolymers, copolymers, such as, for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to, isotactic, syndiotactic and random symmetries.

As used herein, the term "consisting essentially of" does not exclude the presence of additional materials which do not significantly affect the desired characteristics of a given composition or product. Exemplary materials of this sort would include, without limitation, pigments, antioxidants, stabilizers, surfactants, waxes, flow promoters, particulates or materials added to enhance processability of a composition.

SUMMARY OF THE INVENTION

The present invention provides a filter having desirable firmness and pressure drop characteristics for a smoking article. The filter is made from a nonwoven web of a plurality of spunbond fibers or filaments formed to define a plurality of intertwined loop springs. More particularly described, the nonwoven web is made from a plurality of filaments generally having diameters greater than those typically found in spunbond filaments, or greater than about 18–25 microns. The filaments are substantially continuous and intertwined. The filaments are laid randomly onto a moving belt to form a web having a series of interwoven, simple loop springs. Filaments useful in disclosed embodiments have diameters of about 25 to about 100 microns and form intertwined loop springs having diameters of about 0.5–3 millimeters. Desirably, filaments may have diameters of about 25 to about 40 microns and form intertwined loop springs having diameters of about 1–2 millimeters.

It is an object of the present invention to provide a filter made from a nonwoven spunbond web.

It is another object of the present invention to provide a filter for a smoking article formed from a nonwoven spunbond web composed of a series of interwoven, simple loop springs.

It is another object of the present invention to provide a filter having desirable firmness and pressure drop properties for smoking articles, the filter made from a nonwoven spunbond web of a plurality of continuous intertwined filaments, each filament having a diameter of about 25 to about 100 microns, the filaments randomly laid to define intertwined, simple loop springs, each spring having a diameter of about 0.5 to 3 millimeters.

DETAILED DESCRIPTION OF THE PREFERRED EMBODIMENT

While the invention will be described in connection with preferred embodiments, it will be understood that it is not intended to limit the invention to those embodiments. On the contrary, it is intended to cover all alternatives, modifications and equivalents as may be included within the spirit and scope of the invention as defined by the appended claims.

Figure 1:
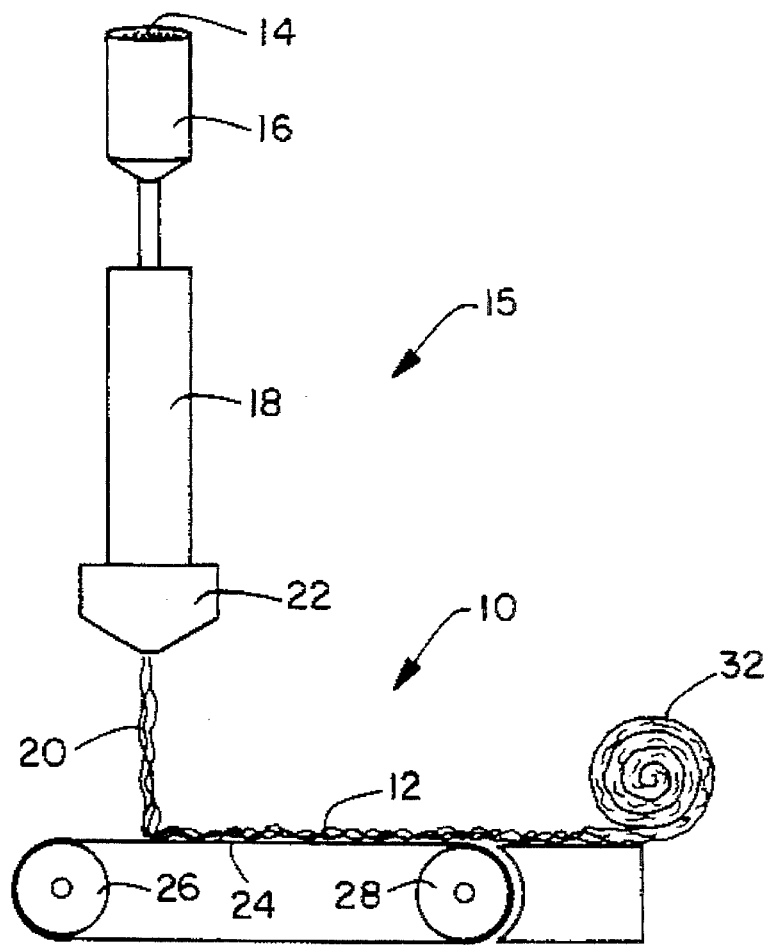
FIG. 1 is a schematic illustration of an exemplary apparatus for manufacturing a nonwoven web of spunbond filaments.

Turning to FIG. 1, there is shown a web forming machine 10 for forming a spunbond web 12 formed of a plurality of substantially continuous filaments. The web forming machine 10 includes a spunbond station 15 having a supply container 16 which holds a supply of polymer 14. The supply container 16 in the spunbond station 15 feeds into a conventional extruder 18. The polymer is heated and extruded 18 in the form of filaments through a plurality of holes in a spinnerette (not shown). The spun filaments are drawn by means of a take-off device 22.

The drawn, continuous filaments 20 are deposited in a substantially random manner as simple loop springs intertwined on a moving, endless foraminous carrier belt 24 driven over spaced-apart rolls 26 and 28, thereby forming the web 12. As discussed below and, in particular, in Appel et al, U.S. Pat. No. 4,340,563, a spunbond process may be adapted to form such loop springs in response to controllable factors including, for example, filament diameter, filament quench rate, and polymer type. An appropriate suction means (not illustrated) can be present to assist the web formation on the carrier belt 24. The web 12 is formed into a roll 32.

The spunbond station 15 may be a conventional extruder with one or more spinnerettes which form continuous filaments of a polymer and deposit those filaments onto the carrier belt 24 in a random interlaced fashion to form loop springs. The spunbond station 15 may include one or more spinnerette heads depending on the speed of the process and the particular polymer being used.

Spunbond materials prepared with continuous filaments generally have at least three common features. First, the polymer is continuously extruded through a spinnerette to form discrete filaments. Second, the filaments are thereafter drawn either mechanically or pneumatically, without breaking, in order to molecularly orient the polymer filaments and achieve tenacity. Third, the continuous filaments are deposited in a substantially random manner onto the carrier belt to form a web.

Conventional nonwoven webs of spunbond filaments generally have filament diameters between about 18 and 25 microns. Conventional webs of such filaments are subsequently bonded (e.g., thermally bonded) to provide a coherent fabric. Filament diameters larger than 25 micron have generally been considered lacking in characteristics desirable for commercial nonwoven fabrics, and operating conditions are adjusted to reduce or eliminate production of such large diameter spunbond filaments.

As discussed above, one common deficiency of previous attempts to form cigarette filters from conventional thermoplastic filament webs have included inadequate firmness so that the filter end of the cigarette has an uncharacteristic and undesirable softness. Another deficiency is a greater than desired pressure drop so that the smoker experiences a perceivable increase in draw resistance.

According to the present invention, unbonded nonwoven webs made with spunbond filaments having diameters greater than 25 microns and which are arrayed in looping spring configuration have been found useful as filter material which provides a desirable level of firmness and pressure drop. Generally speaking, parameters such as the pressure differential in the quench chamber, the polymer flow rate, and the forming distance, are varied according to the polymer being extruded so as to produce the desired filament diameter.

Figure 2:
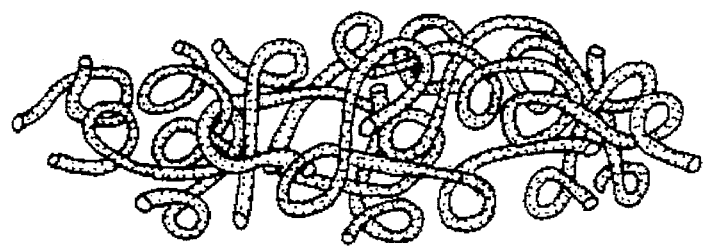
FIG. 2 is a partial section perspective illustration of an exemplary spunbond web.

FIG. 2 is a partial section illustration of the web 12 in perspective view. The discrete, continuous filaments are randomly deposited in simple loops and intertwined in the web. The filaments composing the web 12 are unbonded and free to slide relative to one another.

Figure 3:
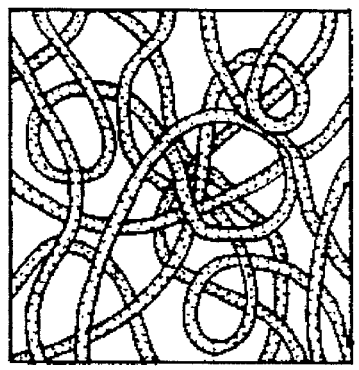
FIG. 3 is an illustration of a planar section of an exemplary spunbond web.
Figure 4:
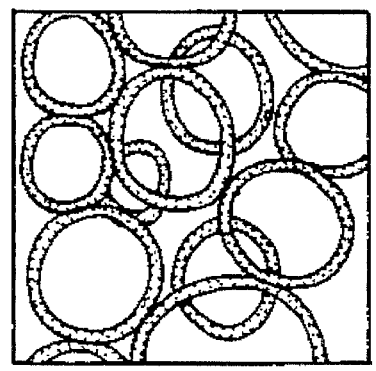
FIG. 4 is an abstraction of the geometry of the filaments forming the web illustrated in FIG. 3.

FIG. 3 illustrates a plane of the web such as that shown in FIG. 2. The filaments are arrayed in the plane of the web as an endless series of simple loops or hitches. By abstraction, this geometry suggests that the spunbond web can be considered to be a collection of circular hoops or springs, as illustrated in FIG. 4. Although the inventors should not be held to a particular theory of operation, it is believed that the circular springs resist deformation and help to prevent collapse of the fabric when a web of filaments is crumpled to make a filter rod.

Figure 5:
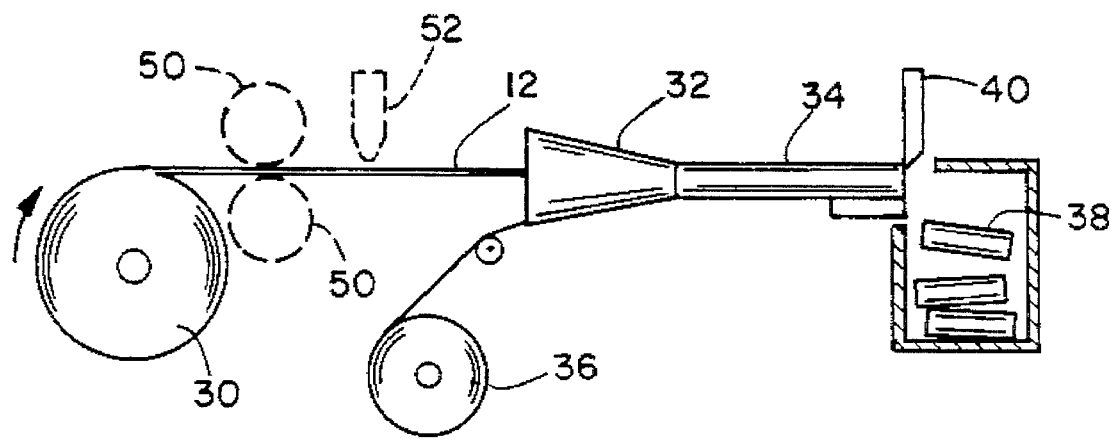
FIG. 5 is a schematic illustration of an exemplary method of forming a web into a filter rod.

As shown schematically in FIG. 5, a roll 30 of the thermoplastic filament web 12 is unwound and drawn into a pre-forming apparatus 32 that gathers or folds the flat web 12 into a cylindrical shape 34 suitable for passage into the filter rod maker. The formed cylinder 34 is usually carried into a rod-making garniture along with a wrapping paper called plug wrap 36 via an endless forming belt (not shown). Prior to entering the garniture, a continuous bead of adhesive is applied to one edge of the plug wrap via an applicator. As these components pass through the garniture, the formed web is compressed into a cylindrical cross-sectional rod while at the same time being enveloped by plug wrap 36. As the adhesive bead contacts the overlap section of wrapped rod, it is sealed by means of a sealing bar. This endless filter rod is then cut into lengths 38 by means of a blade 40.

Figure 6:
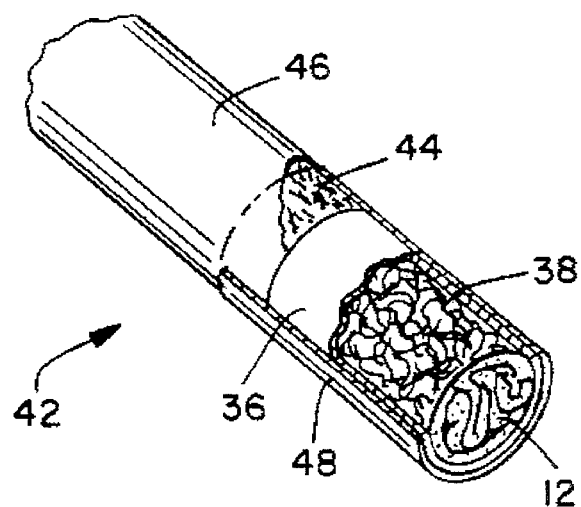
FIG. 6 is a partial perspective view of an exemplary smoking article.

Referring to FIG. 6, a smoking article 42 is partially shown in the form of a cigarette comprising a tobacco rod 44 enclosed by a cigarette wrapper 46 and joined to the filter 38 comprising the web 12 of continuous filaments and the plug wrap 36 by means of a tipping paper strip 48.

Webs made in accordance with the present invention may be pre-treated prior to being formed into a filter rod 38.

Treatments may include, but are not limited to, surface modification treatments, crimping treatments, bonding treatments, thermal treatments and the like. Two exemplary treatments, illustrated in FIG. 5, are a pair of grooved rolls 50 used for crimping and a liquid applicator 52 used for surface treating.

Sample cigarette filters were manufactured from spunbond webs made from a polypropylene polymer and tested. The webs were made using an Exxon commercial grade polypropylene polymer. The webs were manufactured generally in accordance with the teachings of previously referenced U.S. Pat. No. 4,340,563 utilizing a linear drawing system apparatus having a 400 hole die pack. The inlet melt temperature was about 425° F. and throughput was about 0.8 grams of polymer per hole per minute. The die pack temperature was about 430° F. The web basis weight was about 0.8 ounces per square yard (osy) (about 27 grams per square meter). Different filament diameters were obtained by changing the duct pressure differential in the quenching chamber.

Cigarette filters were made from the 0.8 osy (27 gsm) unbonded webs with filament diameters ranging from about 17 to about 39 microns using conventional filter making equipment as illustrated in FIG. 5. The filters were wrapped with a non-porous plug wrap having the trade designation SPW-310 available from Kimberly-Clark Corporation. Filter weight, firmness, and pressure drop tests were conducted on the filters. Each test is described below.

As used herein, the term "filter weight" refers to the measure of the mass of web incorporated into an individual filter. Filter weight is reported as net filter weight (NFW) in units of milligrams per centimeter of filter length minus the weight of the plug wrap paper. Generally speaking, when the materials of the present invention are used in such applications as conventional cigarette filters, the filter weights tend to be less than 80 mg per cm of filter length.

As used herein, the term "firmness" refers to the deflection of a deformable material (e.g., a cigarette filter) in response to an applied force. More particularly, the firmness of cigarette filter samples was measured using an Eastman Firmness Gauge (available from Eastman Chemical Products, Inc., Kingsport, Tenn., division of Eastman Kodak Company). This instrument applies a weight of 350 grams to a test filter. The weight was applied through the shaft of a dial indicator (available from the Federal Products Company, Providence, R.I.) to a circular foot having a diameter of about ½ inch (12.5 millimeters) positioned directly on the filter. The filter is placed below the foot which is lowered to contact the sample without the 350 gram weight being applied to the test filter. The dial indicator is adjusted to have the needle pointing to scale 0. The 350 gram weight is released by an off-set cam and applied to the filter. A reading of the Federal dial is taken after 5 seconds to determine the number of tenths of millimeter deflection. A reading of 10.0 means the test filter has been depressed 1.0 millimeter by the 350 gram weight. Generally speaking, a test result of between about 3 to 8 (i.e., 0.3 to 0.8 millimeter deflection) is a desirable range for cigarette filters. More desirably, the test result is between 4 to 8 (i.e., 0.3 to 0.8 millimeter deflection).

As used herein, the term "filter pressure drop" refers to the amount of vacuum (expressed in centimeters of water) required to draw approximately 1050 cm³/min of air through the filter. Generally speaking, the pressure drop is expressed in centimeters of water and may be normalized to unit length of filter by dividing by the actual filter length. In accordance with the invention, the pressure drop of a filter is desirably in the range of 1.0 to 4.5 cm water/cm filter length. More desirably, the pressure drop is in the range of from about 1.5 to 3.5 cm water/cm filter length.

Circumference of the each filter was measured with a Filtrona Model MTG 102 Tape Gauge available from Fidus Instruments Corporation of Richmond, Va.

Table 1 below reports the test results of the cigarette filter made from the spunbond webs having filament diameters ranging from 17–39 microns as described above. The net filter weight (NFW) is reported in milligrams per centimeter of filter length (minus the filter wrap). The pressure drop is reported in centimeters of water per centimeter of filter length. The firmness is reported as millimeters of deflection.

TABLE 1

| Sample | Filament Diameter (microns) | Plug Wrap | NFW (mg/cm) | Press Drop* | Firm | Circ. (mm) |
|--------|-----------------------------|-----------|-------------|-------------|------|------------|
| A | 16–17 | SPW-310 | 75 | 8.9 | 4.7 | 24.4 |
| B | 22–23 | SPW-310 | 71 | 5.1 | 7.8 | 24.4 |
| C | 24–25 | SPW-310 | 70 | 3.8 | 7.6 | 24.4 |
| D | 29–30 | SPW-310 | 71 | 3.5 | 7.2 | 24.2 |
| E | 38–39 | SPW-310 | 73 | 2.2 | 7.3 | 24.2 |

*cm of water/cm of filter length

Based on the data in Table 1, it is expected that plugs D & E would provide a filter for a smoking article having adequate firmness and acceptable pressure drop. Plug A & B exhibit a pressure drop that is considered excessive for typically available smoking articles. Although filters with a lower pressure drop with more firmness are considered more desirable, the embodiment of C would be useful as a filter for a non-typical smoking article.

While it is not desired to limit the invention to any particular theory, one possible explanation for the resulting desirable plug firmness and pressure drop may be understood by considering that the spunbond filaments comprising the web behave as a collection of circular hoops or springs such as illustrated in FIG. 4. When such a web is reconfigured to make a filter rod, the resistance to deformation of these circular springs prevents collapse of the filter.

It is known from mechanics that the resistance to deformation or stiffness (S) of such springs is proportional with the fourth power of the filament diameter (d) and inversely proportional with the third power of the circular spring diameter (D), i.e., $$S = kd^4/D^3 \qquad (Eq. 1)$$

where k is a proportionality constant which incorporates the filament modulus of the particular polymer used.

Considering that most of the spring diameters (D) are roughly constant in the spunbond webs, this factor can be grouped with the constant k in equation (1) to yield the simple stiffness equation:

$$S = k'd^4 \qquad (Eq. 2)$$

Equation 2 may then be applied to the unbonded webs A through E of Table 2 by dividing each filament diameter by the smallest filament diameter (web A) to yield a normalized diameter. When this is done, a stiffness enhancement can be calculated by merely raising these normalized diameters to the fourth power. The results are shown below.

TABLE 2

| Unbonded Web | Filament Diameter (microns) | Normalized Filament Diameter | Stiffness Enhancement |
| --- | --- | --- | --- |
| A | 17 | 1 | 1 |
| B | 22 | 1.29 | 2.80 |
| C | 25 | 1.47 | 4.68 |
| D | 30 | 1.77 | 9.7 |
| E | 38 | 2.24 | 24.9 |

Such spring analysis can be useful in predicting the behavior of fiber/filament tows used to make conventional cigarette filters. Generally speaking, fiber/filament tows having a high degree of machine direction (MD) orientation are unlikely to have identifiable spring-like structures, much less spring-like structures characterized by relatively uniform small diameters [i.e., if any spring-like structures are present, they are likely to be of very large diameter (D)]. When this information is substituted in Equation 1, the stiffness of the spring structures is calculated to be low because the value of the third power of the circular spring diameter in the denominator would be very large.

This suggests conventional low modulus tows would require artificial stiffening means, such as crimping, to prevent complete collapse of the filter structure and resultant high pressure drop filters. In fact, conventional polypropylene fiber/filament tows usually require crimping treatments in order to produce satisfactory cigarette filters.

Although the inventors should not be held to a particular theory of operation or practice, it is believed that in the manufacture of nonwoven spunbond webs of the present invention, the continuous spunbond filaments should not be "drawn out" by excessive draws in the forming section of the spunbond process. Avoiding excessive draws will generally prevent destruction of the circular spring-like structures (having relatively uniform small diameters) present in the spunbond web produced in accordance with the present invention.

The circular spring structures in the filters of the present invention provides geometric advantages over filter plugs which may be described as column structures. Exemplary filter plugs having columnar structures are disclosed in U.S. Pat. No. 4,961,415 to Radwanski, et al. The stiffness of the filter of the present invention arises from contributions by all of the springs, while in the column structure, only the fraction of columns lying in the web cross direction contribute to the stiffness.

It is contemplated that any thermoplastic polymer suitable for spunbond processing may be used in the practice of the present invention. Desirably, the nonwoven web may be formed from polyesters or polyolefins. Exemplary polyolefins include polyethylene, polypropylene, polybutene, ethylene copolymers, propylene copolymers and butene copolymers. More desirably, the polyolefin is isotatic polypropylene.

Due to the nature of the spunbond thermoforming process, additives (e.g., calcium carbonate) can be easily incorporated internally in the polymer or blown onto the molten polymer surface as the polymer is extruded, in order to change the structure of the spunbond web and thus its performance in a filter element. Also, spunbond webs, after formation, are easily subject to known post treatments with auxiliary agents in dry or liquid form to provide certain organoleptic and/or medicinal attributes.

The resistance to collapse by filters made from the webs according to the present invention has important consequences during the smoking of a filtered cigarette. Such filter plugs are free from the softness or "mushiness" which is perceived as a negative attribute by most smokers. The large diameter spunbond filaments with coil springs provide adequate firmness and acceptable pressure drop.

Thus, there has been provided in accordance with the invention, an improved filter material for smoking articles that satisfies the objects, aims and advantages set forth above. While the invention has been described in conjunction with specific embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the appended claims.

What is claimed is:

1. A filter for a smoking article, said filter comprising a cylinder adapted to fit the smoking article and formed from an unbonded nonwoven web of continuous intertwined spunbond filaments, each having a diameter of about 25 to about 100 microns, the plurality of filaments randomly deposited to define a plurality of intertwined loop springs, each loop spring having a diameter of about 0.5 to 3 millimeters, so that the filter element has a pressure drop of 1 to about 4.5 cm water/cm filter and a firmness value from about 0.3 to 0.8 millimeter deflection.

2. The filter element of claim 1, wherein filaments have a diameter of about 25 to about 40 microns.

3. The filter element of claim 1, wherein the plurality of intertwined loop springs each have a diameter of about 1 to 2 millimeters.

4. The filter element of claim 1, wherein the filter element has a firmness value from about 0.4 to 0.8 millimeter deflection and a pressure drop of about 1.5 to about 3.5 cm water/cm filter.

5. The filter element of claim 1, wherein the filaments are formed from a thermoplastic polymer selected from polyolefins and polyesters.

6. The filter element of claim 5, wherein the filaments are formed from a thermoplastic polyolefin polymer selected from polyethylene, polypropylene, polybutene, ethylene copolymers, propylene copolymers and butene copolymers.

7. The filter element of claim 1, wherein the filter element contains one or more additives distributed throughout the nonwoven spunbond web of continuous intertwined filaments.

8. The filter element of claim 7, wherein the filter element contains one or more additives selected from organoleptic and medicinal additives.

9. A filter for a smoking article, said filter comprising a cylinder adapted to fit the smoking article and formed from an unbonded nonwoven web of continuous intertwined spunbond filaments formed from a thermoplastic polymer selected from polyolefins and polyesters, each filament having a diameter of about 25 to about 100 microns, the filaments defining a plurality of intertwined loop springs, each loop spring having a diameter of about 0.5 to 3 millimeters, so that the filter element has a pressure drop of 1 to about 4.5 cm water/cm filter and a firmness value from about 0.3 to 0.8 millimeter deflection.

10. The filter element of claim 9, wherein filaments have a diameter of about 25 to about 40 microns.

11. The filter element of claim 9, wherein the plurality of intertwined loop springs each have a diameter of about 1 to 2 millimeters.

12. The filter element of claim 9, wherein the filter element has a pressure drop of 1 to about 4.5 cm water/cm filter and a firmness value from about 0.3 to 0.8 millimeter deflection.

13. The filter element of claim 12, wherein the filter element has a firmness value from about 0.4 to 0.8 millimeter deflection and a pressure drop of about 1.5 to about 3.5 cm water/cm filter.

14. The filter element of claim 9, wherein the filaments are formed from a thermoplastic polyolefin polymer selected from polyethylene, polypropylene, polybutene, ethylene copolymers, propylene copolymers and butene copolymers.

15. The filter element of claim 9, wherein the filter element contains one or more additives distributed throughout the nonwoven spunbond web of continuous intertwined filaments.

16. The filter element of claim 15, wherein the filter element contains one or more additives selected from organoleptic and medicinal additives.

* * * * *